(12) United States Patent
Kurumaya et al.

(10) Patent No.: US 8,350,082 B2
(45) Date of Patent: Jan. 8, 2013

(54) PROCESS FOR PRODUCING FLUORINE-CONTAINING COMPOUNDS

(75) Inventors: Mitsuo Kurumaya, Katagami (JP); Tsunetoshi Honda, Akita (JP); Kota Omori, Akita (JP)

(73) Assignees: Mitsubishi Materials Corporation, Tokyo (JP); Mitsubishi Materials Electronic Chemicals Co., Ltd., Akita-Shi (JP)

( * ) Notice: Subject to any disclaimer, the term of this patent is extended or adjusted under 35 U.S.C. 154(b) by 186 days.

(21) Appl. No.: 12/734,842

(22) PCT Filed: Nov. 28, 2008

(86) PCT No.: PCT/JP2008/071654
§ 371 (c)(1),
(2), (4) Date: May 27, 2010

(87) PCT Pub. No.: WO2009/069750
PCT Pub. Date: Jun. 4, 2009

(65) Prior Publication Data
US 2010/0305345 A1     Dec. 2, 2010

(30) Foreign Application Priority Data

Nov. 28, 2007 (JP) ................. 2007-307240
Nov. 28, 2007 (JP) ................. 2007-307241

(51) Int. Cl.
*C07C 51/58* (2006.01)
(52) U.S. Cl. ......... 562/863; 562/840; 562/850; 570/161
(58) Field of Classification Search .......... None
See application file for complete search history.

(56) References Cited

U.S. PATENT DOCUMENTS

| | | | | |
|---|---|---|---|---|
| 2,013,030 A | | 9/1935 | Calcott et al. | |
| 5,093,432 A | * | 3/1992 | Bierschenk et al. | 525/331.6 |
| 6,307,105 B1 | * | 10/2001 | Casteel et al. | 568/393 |
| 2003/0036668 A1 | | 2/2003 | Bowden et al. | |
| 2003/0204099 A1 | | 10/2003 | Okazoe et al. | |
| 2006/0074260 A1 | * | 4/2006 | Kaneko et al. | 562/849 |

FOREIGN PATENT DOCUMENTS

| | | |
|---|---|---|
| EP | 0018606 A1 | 11/1980 |
| JP | 2002-53523 | 2/2002 |
| JP | 2003-531131 | 10/2003 |
| JP | 2006-131620 A | 5/2006 |
| WO | WO-00/56694 A1 | 9/2000 |

OTHER PUBLICATIONS

International Search Resort dated Jan. 27, 2009, issued on PCT/JP2008/071654.
Supplementary European Search Report dated Jan. 20, 2012, issued for the corresponding European patent application No. 08855193.2.
Susumu Misaki, "Hydrofluoric Acid as a Solvent for Direct Fluorination," Chemistry Express, Kinki Chemical Society, JP, vol. 1, No. 11, Jan. 1, 1986, pp. 683-686.

* cited by examiner

*Primary Examiner* — Sudhakar Katakam
(74) *Attorney, Agent, or Firm* — Edwards Wildman Palmer LLP; James E. Armstrong, IV; Nicholas J. DiCeglie, Jr.

(57) ABSTRACT

This process for producing fluorine-containing compounds includes liquid-phase fluorination by introducing a raw material compound and fluorine gas into a solvent to replace hydrogen atoms in the raw material compound with fluorine atoms. More specifically, the process for producing fluorine-containing compounds includes (1) promoting fluorination by dissolving the raw material compound in anhydrous hydrofluoric acid and introducing into a liquid-phase fluorination solvent, or (2) promoting fluorination by dissolving the raw material compound in a perfluoro compound having a plurality of polar groups in a molecule thereof and introducing into a liquid-phase fluorination solvent. According to these processes, a fluorination reaction can be carried out at high yield and without containing hardly any isomers while using a hydrocarbon compound as is for the raw material.

10 Claims, No Drawings

PROCESS FOR PRODUCING FLUORINE-CONTAINING COMPOUNDS

TECHNICAL FIELD

The present invention relates to a process for producing fluorine-containing compounds. More particularly, the present invention relates to a process for producing perfluoro compounds by fluorination of hydrocarbon compounds.

The present application claims priority on Japanese Patent Application No. 2007-307240 filed in Nov. 28, 2007 and on Japanese Patent Application No. 2007-307241 filed on Nov. 28, 2007, the contents of which are incorporated herein by reference.

BACKGROUND ART

Fluorine-containing compounds, and particularly perfluoro compounds in which all hydrogen atoms of a hydrocarbon compound have been replaced with fluorine, have unique properties such as chemical stability and water and oil repellency, and are expected to be used in various applications such as pharmaceuticals, agricultural chemicals, polymers, functional products, surfactants, cleaners and various other chemical products and synthetic intermediates thereof.

A typical known example of a process for producing perfluoro compounds is electrolytic fluorination. Electrolytic fluorination is a process in which a raw material compound and hydrogen fluoride are placed in an electrolytic cell and current is applied between electrodes to carry out a fluorination reaction that uses hydrogen fluoride for the fluorine source. However, electrolytic fluorination requires considerable equipment costs. In addition, the raw material compound is susceptible to the occurrence of cleavage of carbon-carbon bonds and isomerization during reaction of the raw material compound with hydrogen fluoride, thereby making it difficult to obtain a target compound at high purity and high yield.

In addition, other known examples of processes for producing fluorine-containing compounds include a process that uses fluorine gas in a vapor phase, and a process that uses a higher metal fluoride produced from a metal fluoride and fluorine gas. However, these conventional fluorination processes were associated with difficulties in controlling the reaction due to the violent reactivity of fluorine gas as well as difficulty in handling the fluorine gas.

"Liquid-phase fluorination" has been proposed as a modified process for fluorinating the raw material compounds. "Liquid-phase fluorination" uses a perfluorocarbon for the solvent, and continuously supplies fluorine gas and a raw material diluted with the solvent in a state in which the solvent is saturated with the fluorine gas by dissolving the fluorine gas therein (Patent Document 1). According to this process, fluorination can be carried out while inhibiting a decomposition reaction of the raw material. However, in order to use the solvent with fluorine dissolved therein, the solvent is limited to a perfluorocarbon that is stable in fluorine. Thus, those compounds able to be fluorinated with this process are limited to those that dissolve in perfluorocarbons. Consequently, it is difficult to apply this process to ordinary hydrocarbon compounds to the poor solubility thereof.

Therefore, a process has been proposed in which an ester compound that easily dissolves in perfluorocarbons is synthesized by a reaction between an alcohol and a perfluorocarbonyl compound (see formula (I) below), followed by carrying out fluorination in the liquid phase using the resulting ester compound for the raw material (see formula (II) below) (Patent Document 2). By thermally decomposing the perfluoro compound obtained in formula (II) below with a nucleophile, a perfluoroacyl compound can be obtained that is derived from the raw material alcohol (see formula (III) below).

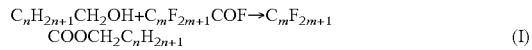

(I)

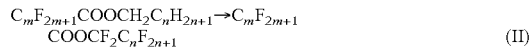

(II)

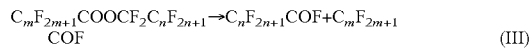

(III)

According to this process, even in the case of a higher alcohol that does not dissolve in perfluorocarbon as is, a liquid-phase fluorination reaction can be applied since the higher alcohol can be solubilized by esterifying with perfluorocarboxylic acid fluoride. On the other hand, the raw material in this process is limited to an esterifiable alcohol. In addition, an expensive perfluorocarbonyl compound is required. Moreover, a step for synthesizing ester, a step for separating the fluorination product, as well as decomposition and separation steps are required.

A process has also been proposed for fluorinating a raw material that does not dissolve in a fluorination reaction solvent in a liquid phase and in the presence of a substrate (such as benzene) that rapidly accelerates fluorination reactions by itself (Patent Document 3). According to this process, a fluorination reaction can be provided that uses a hydrocarbon compound for the raw material as is without using an expensive perfluorocarbonyl compound. In addition, pre-treatment or post-treatment steps such as esterification, decomposition or the like are not required. However, expenses are incurred for the added fluorination reaction substrate. What is more, since excess fluorine is consumed for fluorination and by-products are generated attributable to consumption of the excess fluorine, a step is necessary for removing those by-products. In addition, raw material compounds to which this process can be applied are limited to compounds such as highly chlorinated compounds that hardly react at all with fluorine gas even if introduced undiluted into the reaction atmosphere.

[Patent Document 1] U.S. Pat. No. 5,093,432
[Patent Document 2] WO 00/56694
[Patent Document 3] Japanese Unexamined Patent Application, First Publication No. 2006-131620

DISCLOSURE OF INVENTION

Problems to be Solved by the Invention

The present invention solves the aforementioned problems of the prior art. An object of the present invention is to provide a process for fluorinating various organic compounds, and particularly, a process for safely realizing perfluorination of various organic compounds at high yield without converting the primary structure of the hydrocarbon compound raw material.

Means for Solving the Problems

During the course of examining the aforementioned problems, the following finding was made during liquid-phase fluorination of organic compounds. An organic compound is preliminarily dissolved in anhydrous hydrofluoric acid or a perfluoro compound having a plurality of polar groups in a molecule thereof. If an anhydrous hydrofluoric acid solution or perfluoro compound solution of this organic compound is then introduced into a fluorination solvent, perfluorination can be realized safely and at high yield without converting the primary structure of a hydrocarbon compound raw material. The present invention is based on this finding.

According to the present invention, a process for producing fluorine-containing compounds is provided that is comprised in the manner described below.

(1) A process for producing fluorine-containing compounds, includes liquid-phase fluorination by introducing a raw material compound and fluorine gas into a solvent to replace hydrogen atoms in the raw material compound with fluorine atoms, wherein, fluorination is promoted by dissolving the raw material compound in anhydrous hydrofluoric acid and introducing into a liquid-phase fluorination solvent.

(2) A process for producing fluorine-containing compounds, includes liquid-phase fluorination by introducing a raw material compound and fluorine gas into a solvent to replace hydrogen atoms in the raw material compound with fluorine atoms, wherein, fluorination is promoted by dissolving the raw material compound in a perfluoro compound having a plurality of polar groups in a molecule thereof and introducing into a liquid-phase fluorination solvent.

(3) The process for producing fluorine-containing compounds described in (2) above, wherein the perfluoro compound having a plurality of polar groups in a molecule thereof (to be referred to as the raw material solution) is a compound having a plurality of carbonyl groups or sulfonyl groups in a molecule thereof.

(4) The process for producing fluorine-containing compounds described in (2) or (3) above, wherein the raw material solution is an $XOCYCOX$, $XO_2SYCOX$ or $XO_2SYSO_2X$ compound (wherein, X represents a halogen and Y represents a linear or branched perfluoroalkylene group).

(5) The process for producing fluorine-containing compounds described in any of (1) to (4) above, wherein the liquid-phase fluorination solvent is a perfluorohydrocarbon solvent (which may contain heteroatoms in a molecule thereof).

(6) The process for producing fluorine-containing compounds described in any of (2) to (5) above, wherein the liquid-phase fluorination solvent is a perfluoro compound having a plurality of polar groups in a molecular thereof.

(7) The process for producing fluorine-containing compounds described in any of (1) to (6) above, wherein liquid-phase fluorination is carried out after preliminarily dissolving fluorine gas in the liquid-phase fluorination solvent.

(8) The process for producing fluorine-containing compounds described in any of (1) to (7) above, wherein the liquid-phase fluorination is carried out in the presence of a linear, branched or cyclic hydrocarbon compound (which may contain a heteroatom in a molecule thereof) having 1 or more unsaturated bonds or 1 or more C—H bonds in a molecule thereof and having 5 or more carbon atoms and 30 or less carbon atoms.

(9) The process for producing fluorine-containing compounds described in any of (1) to (8) above, wherein the raw material compound is an organic acid or organic acid halide.

EFFECTS OF THE INVENTION

According to the process of the present invention, fluorine-containing compounds can be obtained at high yield. In addition, fluorine-containing compounds produced according to the process of the present invention generate hardly any isomers. Moreover, the process of the present invention allows the reaction to proceed unexpectedly mildly.

Moreover, according to the process of the present invention, a fluorination reaction can be carried out using a hydrocarbon compound for the raw material as is by diluting with inexpensive anhydrous hydrofluoric acid without using an expensive perfluorocarbonyl compound as a raw material. In addition, even in the case of using a perfluorocarbonyl compound as an auxiliary solvent, a fluorination reaction can still be carried out using a hydrocarbon compound for the raw material. In addition, pre-treatment or post-treatment in the form of esterification or decomposition is not required as in the prior art, and it is not necessary to add excessive added materials.

BEST MODE FOR CARRYING OUT THE INVENTION

The following provides a detailed explanation of the present invention using embodiments thereof.

The production process of the present invention includes liquid-phase fluorination in which a raw material compound and fluorine gas are introduced into a solvent to replace hydrogen atoms of the raw material compound with fluorine atoms. More specifically, the production process of the present invention relates to a process for producing fluorine-containing compounds comprising promoting fluorination by dissolving a raw material compound in anhydrous hydrofluoric acid and introducing into a liquid-phase fluorination solvent (first embodiment), or promoting fluorination by dissolving a raw material compound in a perfluoro compound having a plurality of polar groups in a molecule thereof (raw material solution) and introducing into a liquid-phase fluorination solvent (second embodiment).

First Embodiment

In the first embodiment, a raw material compound and fluorine gas are introduced into a solvent to carry out liquid-phase fluorination in which hydrogen atoms in the raw material compound are replaced with fluorine atoms, wherein fluorination is promoted by dissolving the raw material compound in anhydrous hydrofluoric acid followed by introducing into the liquid-phase fluorination solvent.

[Raw Material Compound]

In the first embodiment, the raw material compound is used dissolved in anhydrous hydrofluoric acid. Examples of raw material compounds able to be dissolved in anhydrous hydrofluoric acid that are also organic compounds containing hydrogen include aromatic hydrocarbons, alcohols, ethers, organic acids, esters and acid halides.

The alcohols, ethers, organic acids, esters and acid halides may contain a plurality of functional groups (which may be the same or different) in a molecule thereof. Carboxylic acids and polycarboxlyic acids such as dicarboxylic acids, along with halides thereof, are highly soluble in anhydrous hydrofluoric acid, and can be used particularly preferably in the first embodiment. In addition, in cases in which reaction with fluorine is permitted, double bonds or other unsaturated bonds as well as heteroatoms such as nitrogen or sulfur may also be contained. Although there are no particular limitations on the number of carbon atoms of the raw material compound, the number of carbon atoms is normally not lower than 2 and not greater than 14. In particular, raw material compounds having 2 or more and 10 or less carbon atoms and which are a liquid or solid at room temperature can be applied preferably.

In addition, among the raw material compounds, organic compounds that contain hydrogen may also be compounds that react in some manner during contact with anhydrous hydrofluoric acid provided they do not undergo fluctuations in the carbon framework thereof. For example, acid chlorides can be transformed to acid fluorides during contact with anhydrous hydrofluoric acid. However, since this reaction does not cause fluctuations in the carbon framework, these compounds can be used in the first embodiment. Examples of acid chlorides include caprylyl chloride, sebacoyl chloride, suberoyl chloride and adipoyl chloride.

[Dissolution in Anhydrous Hydrofluoric Acid]

Dissolution in anhydrous hydrofluoric acid is carried out by either mixing in the entire amount of the raw material compound while cooling the anhydrous hydrofluoric acid (at about 0° C.), or by adding one to the other a little at a time. Dissolution and concentration are typically carried out in a reaction vessel made of a material that is resistant to anhydrous hydrofluoric acid.

There are no limitations on the mixing ratio between the anhydrous hydrofluoric acid and the raw material compound. The anhydrous hydrofluoric acid is preferably added at not lower than 0.5 mol and not greater than 100 mol, and more preferably at not lower than 1 mol and not greater than 30 mol, based on 1 mol of the raw material compound.

If the amount of anhydrous hydrofluoric acid is excessively large with respect to the raw material compound, it is necessary to use a large amount of hydrofluoric acid scavenger corresponding to the amount thereof, while also making handling of the raw material solution difficult. If the amount of anhydrous hydrofluoric acid is excessively small with respect to the raw material compound, it becomes difficult to control the supply of raw material solution, thereby making the procedure dangerous.

[Liquid-Phase Fluorination Solvent]

An anhydrous hydrofluoric acid solution of the raw material compound is added to the liquid-phase fluorination solvent. The liquid-phase fluorination solvent is an organic solvent that does not substantially react with fluorine, the solubility of fluorine gas therein is comparatively high, and is a liquid under the fluorination conditions. Examples of such solvents include perfluorohydrocarbons such as perfluoroalkanes and perfluorocycloalkanes.

The perfluoroalkanes preferably have, for example, about not lower than 4 and not greater than 18 carbon atoms. More preferably, the perfluoroalkanes are linear or branched perfluoroalkanes having about not lower than 5 and not greater than 12 carbon atoms that are liquids at room temperature. Specific examples include perfluoropentane, perfluorohexane, perfluoroheptane, perfluorooctane, perfluorononane and perfluorodecane. The perfluorocycloalkanes preferably have, for example, about not lower than 5 and not greater than 18 carbon atoms and more preferably about not lower than 5 and not greater than 12 carbon atoms. Specific examples include perfluorocyclopentane, perfluorocyclohexane, perfluorocycloheptane and perfluorocyclooctane. The rings thereof may have substituents (such as a perfluoroalkyl group).

These perfluorohydrocarbon compounds may contain a heteroatom such as oxygen or nitrogen in a molecule thereof. Examples include perfluoroamines such as perfluorotributylamine, perfluoroethers such as perfluorobutyl tetrahydrofuran or perfluoropolyether, and perfluoroacid fluoride.

Among the aforementioned solvents, although perfluoroalkanes, perfluorocycloalkanes, perfluoroethers, perfluoroalkylamines and perfluoroacid fluoride are preferable, the specific solvent is determined according to the target compound.

There are no limitations on the amount of solvent used. The amounts of solvent is suitably not lower than 1 time and not greater than 500 times, preferably not lower than 10 times and not greater than 500 times, and more preferably not lower than 20 times and not greater than 200 times the weight of the raw material in the anhydrous hydrofluoric acid. Fluorine is preferably dissolved in the solvent in advance. If the amount of solvent is too low, a tendency such as a decrease in molar yield of the perfluoro compound obtained from the reaction or an increase in by-products is observed. In addition, if the amount of solvent added is too high, costs tend to increase due to factors such as a decrease in batch yield, increased time and labor required for separation and excess fluorine gas.

[Liquid-Phase Fluorination Reaction]

The liquid-phase fluorination reaction is carried out by preliminarily dissolving fluorine in the solvent, and blowing in fluorine gas in an amount that corresponds to the amount of hydrogen in the raw material compound present in the supplied hydrofluoric acid solution. Although the fluorine gas may be used without diluting, it is preferably used mixed with an inert gas from the viewpoint of safety. Although examples of inert gas include nitrogen gas, argon gas and helium gas, nitrogen gas is preferable from the viewpoint of cost. Although there are no limitations on the concentration of fluorine gas in the mixed gas, it is preferably 50% by volume or less, more preferably 5% or more and 40% or less by volume and even more preferably 10% or more and 30% or less by volume. If the concentration of fluorine gas is excessively high, the reaction may proceed violently, while if the concentration of fluorine gas is excessively low, the reaction does not proceed sufficiently. In addition, the amount of fluorine gas blown in is not lower than 0.5 times moles and not greater than 10 times moles, preferably not lower than 0.8 times moles and not greater than 5 times moles, and more preferably not lower than 1 times moles and not greater than 4 times moles the amount of hydrogen in the raw material. If the amount of fluorine is low, side reactions increase due to accumulation of the raw material hydrocarbon, while if the amount of fluorine is high, fluorine, which is one of the raw materials, is wasted.

Although varying according to the type of solvent, the fluorination temperature is preferably −50° C. or more and 50° C. or less, more preferably −10° C. or more and 40° C. or less and even more preferably 0° C. or more and 30° C. or less. The raw material solution and hydrofluoric acid generated as a by-product accompanying the reaction are preferably removed outside the reaction system.

The raw material hydrocarbon compound is dissolved in anhydrous hydrofluoric acid, and this anhydrous hydrofluoric acid solution is reacted with fluorine gas in a solvent. As a result, a perfluoro compound is obtained according to the following reaction formulas [1] and [2] in which hydrogen of the raw material compound is replaced with fluorine.

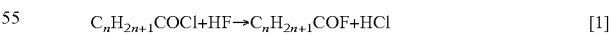

$$C_nH_{2n+1}COCl + HF \rightarrow C_nH_{2n+1}COF + HCl \quad [1]$$

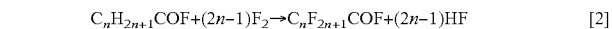

$$C_nH_{2n+1}COF + (2n-1)F_2 \rightarrow C_nF_{2n+1}COF + (2n-1)HF \quad [2]$$

Furthermore, during the aforementioned fluorination reaction, a linear, branched or cyclic hydrocarbon compound having 5 or more carbon atoms and 30 or less carbon atoms and one or more unsaturated bonds or one or more C—H bonds in a molecule thereof (and which may also contain a heteroatom such as oxygen, nitrogen or fluorine in a molecule thereof) may also be present. Examples of such compounds include aliphatic hydrocarbons such as pentane, hexane, hexene, cyclohexane or cyclohexene, ethers such as diethyl ether or tetrahydrofuran, esters such as ethyl acetate and aromatic hydrocarbons such as benzene or toluene.

These compounds may also be partially substituted with fluorine. Examples include ethers and esters, in which a portion of the constituents are pet-fluorinated while the other moieties are not substituted with fluorine in the manner of hexafluoroisopropyl methyl ether or 1,1,2,2,3,3-hexafluoropropyl ethyl ether, aromatic hydrocarbons in which substituents or hydrogens present on rings of compounds such as fluorobenzene, trifluoromethylbenzene or 4-florotrimethylbenzene are partially fluorinated. All hydrogen atoms of aromatic hydrocarbons may also be completely substituted with fluorine in the manner of hexafluorobenzene.

Although there are no particular limitations on the amounts of these added substances, the amount thereof is preferably equal to or more than 0.005 times and equal to or lower than 5 times, more preferably equal to or more than 0.05 times and equal to or lower than 3 times, and even more preferably equal to or more than 0.1 times and equal to or lower than 0.5 times the raw material compound in terms of the molar ratio thereof. If the added amount is excessively high, the amount of fluorine gas consumed in reactions with these compounds increases, and the amounts of by-products also increase. These added substances may be added to the anhydrous hydrofluoric acid solution of the raw material compound at any time prior to the liquid-phase fluorination reaction. In addition, these added substances may also be added to a reaction mixture of the raw material compound anhydrous hydrofluoric acid solution and the liquid-phase fluorination solvent during the liquid-phase fluorination reaction.

The liquid-phase fluorination reaction indicated in the first embodiment is carried out in a reaction vessel made of a material that is resistant to anhydrous hydrofluoric acid. Hydrogen fluoride generated by the reaction is preferably removed by either having a hydrogen fluoride scavenger present in the reaction system or by filling a hydrogen fluoride scavenger into an exhaust gas pathway. An alkaline metal fluoride such as sodium fluoride or potassium fluoride is preferable for the hydrogen fluoride scavenger, and sodium fluoride is particularly preferable.

Second Embodiment

In the second embodiment, a raw material compound and fluorine gas are introduced into a solvent to carry out liquid-phase fluorination in which hydrogen atoms in the raw material compound are replaced with fluorine atoms, wherein fluorination is promoted by dissolving the raw material compound in a perfluoro compound (raw material solution) having a plurality of polar groups in a molecule thereof followed by introducing into a liquid-phase fluorination solvent. In addition, liquid-phase fluorination can also be carried out by using the perfluoro compound having a plurality of polar groups in a molecule thereof as a solvent.

[Raw Material Compound]

In the second embodiment, the raw material is used after dissolving in a perfluoro compound having a plurality of polar groups in a molecule thereof (to be referred to as the raw material solution). Examples of raw material compounds that can be dissolved in the raw material solution include alkanes, cycloalkanes, aromatic hydrocarbons, alcohols, ethers, organic acids, esters and acid halides. The alcohols, ethers, organic acids, esters and acid halides may contain a plurality of functional groups (which may be the same or different) in a molecule thereof. Carboxylic acid, polycarboxylic acids such as dicarboxylic acids and halides thereof are highly soluble in the raw material solution, and can be applied particularly preferably in the second embodiment. In addition, in cases in which reaction with fluorine is permitted, double bonds or other unsaturated bonds as well as heteroatoms such as nitrogen or sulfur may also be contained. Although there are no particular limitations on the number of carbon atoms of the raw material compound, the number of carbon atoms is normally not lower than 2 and not greater than 14. In particular, raw material compounds having 2 or more and 10 or less carbon atoms and which are a liquid or solid at room temperature can be applied preferably.

[Raw Material Solution]

Examples of the raw material solution include compounds having a plurality of carbonyl groups or sulfonyl groups in a molecule thereof. More particularly, compounds having the chemical structures indicated in formulas [3] to [5] below are included (wherein, X represents a halogen, and Y represents a linear or branched perfluoroalkylene group).

$$XOCYCOX \quad [3]$$

$$XO_2SYCOX \quad [4]$$

$$XO_2SYSO_2X \quad [5]$$

There are no particular limitations on Y provided the raw material solution is a liquid at the temperature of the fluorination reaction. A compound normally having 1 or more carbon atoms and 16 or less carbon atoms, preferably 1 or more carbon atoms and 12 or less carbon atoms and more preferably 1 or more carbon atoms and 8 or less carbon atoms is preferable. Examples of X include halogens such as chlorine and fluorine. Furthermore, fluorine is preferable from the viewpoint of preventing the generation of chlorination by-products. Such compounds can be produced by electrolytic fluorination and the like, and such compounds can also be used in the second embodiment.

[Dissolution in Raw Material Solution]

Dissolution is carried out either by mixing in the entire amount of the raw material compound or by adding one to other a little at a time, while holding at a temperature equal to or lower than the boiling point of the raw material solution. Dissolution and concentration are carried out in a reaction vessel made of a material that is resistant to the raw material solution.

There are no limitations on the mixing ratio of the raw material solution and the raw material compound. The raw material solution is preferably added at an equal amount of the weight of the raw material compound or more and 100 times or less the amount of the weight of the raw material compound, and more preferably at 5 times or more and 50 times or less the amount of the weight of the raw material compound.

If the amount of the raw material solution relative to the raw material compound is excessively large, excessive time and labor are required for separation following the reaction. If the amount of the raw material solution relative to the raw material compound is excessively small, it becomes difficult to control dissolution, thereby making the procedure dangerous.

[Liquid-Phase Fluorination Solvent]

The aforementioned solution of the raw material compound is added to the liquid-phase fluorination solvent. The liquid-phase fluorination solvent is an organic solvent that does not substantially react with fluorine, the solubility of fluorine gas therein is comparatively high, and is a liquid under the reaction conditions. Examples of such solvents include the perfluorohydrocarbons such as perfluoroalkanes and perfluorocycloalkanes indicated in the first embodiment. In addition, perfluoro compounds having a plurality of polar groups can also be used for the liquid-phase fluorination solvent.

Specific examples of perfluoroalkanes include the same perfluoroalkanes as those indicated in the first embodiment. Specific examples of perfluorocycloalkanes include the same perfluorocycloalkanes as those indicated in the first embodiment.

Specific examples of perfluorohydrocarbon compounds other than perfluoroalkanes and perfluorocycloalkanes are the same as those indicated as specific examples in the first embodiment.

In addition, preferable examples of solvents include the same solvents indicated as specific examples in the first embodiment.

There are no limitations on the amount of solvent used. The amounts of solvent is suitably not lower than 1 time and not greater than 500 times, preferably not lower than 10 times and not greater than 500 times, and more preferably not lower than 20 times and not greater than 200 times the weight of the raw material. Fluorine is preferably dissolved in the solvent in advance.

If the amount of solvent is excessively low, a tendency such as a decrease in molar yield of the perfluoro compound obtained from the reaction or an increase in by-products is observed. In addition, if the amount of solvent added is too high, costs tend to increase due to factors such as a decrease in batch yield, increased time and labor required for separation and excess fluorine gas.

[Liquid-Phase Fluorination Reaction]

The liquid-phase fluorination reaction is carried out by preliminarily dissolving fluorine in the solvent, and blowing in fluorine gas in an amount that corresponds to the amount of hydrogen in the raw material compound present in the supplied raw material solution. The method for using the fluorine gas, examples of inert gases mixed with the fluorine gas, and the concentration of fluorine gas in the mixed gas of the fluorine gas and an inert gas are preferably the same as the examples indicated in the first embodiment.

The amount of fluorine blown in and the fluorination temperature are preferably the same as the examples indicated in the first embodiment.

Hydrofluoric acid generated as a by-product accompanying the reaction is preferably removed outside the reaction system.

The raw material hydrocarbon compound is dissolved in the aforementioned raw material solution, and as a result of reacting this solution with fluorine gas in a solvent, a perfluoro compound is obtained according to the following reaction formula [6] in which hydrogen of the raw material compound is replaced with fluorine.

$$C_nH_{2n+1}COCl \rightarrow C_nF_{2n+1}COF \quad [6]$$

Furthermore, during the aforementioned fluorination, a linear, branched or cyclic hydrocarbon compound having 5 or more carbon atoms and 30 or less carbon atoms and one or more unsaturated bonds or one or more C—H bonds in a molecule thereof (and which may also contain a heteroatom such as oxygen, nitrogen or fluorine in a molecule thereof) may also be present. Examples of such compounds include the same compounds as the examples indicated in the first embodiment. In addition, these compounds may be partially substituted with fluorine in the same manner as the examples indicated in the first embodiment.

Although there are no particular limitations on the amounts of these added substances, the amount thereof is preferably equal to or more than 0.005 times and equal to or lower than 5 times, more preferably equal to or more than 0.05 times and equal to or lower than 3 times, and even more preferably equal to or more than 0.1 times and equal to or lower than 1 time the raw material compound in terms of the molar ratio thereof. If the added amount is excessively high, the amount of fluorine gas consumed in reactions with these compounds increases, and the amounts of by-products also increase. These added substances may be added to the solution of the raw material compound at any time prior to the liquid-phase fluorination reaction. In addition, these added substances may also be added to a reaction mixture of the raw material compound solution and the liquid-phase fluorination solvent during the liquid-phase fluorination reaction.

The liquid-phase fluorination reaction indicated in the second embodiment is normally carried out in a reaction vessel made of a material that is resistant to fluorine gas. Hydrogen fluoride generated by the reaction is recovered and removed with a condenser and the like. Alternatively, hydrogen fluoride is recovered by having a hydrogen fluoride scavenger present in the reaction system. In addition, hydrogen fluoride may be removed by filling a hydrogen fluoride scavenger into an exhaust gas pathway. An alkaline metal fluoride such as sodium fluoride or potassium fluoride is preferable for the hydrogen fluoride scavenger, and sodium fluoride is particularly preferable. Following completion of the reaction, fluorine gas is removed from the reaction system by blowing in an inert gas and the like. The reaction product, raw material solution and liquid-phase fluorination solvent are separated and recovered by fractional distillation and the like. The solvents can each be reused.

According to the production processes indicated in the first and second embodiments as described above, target compounds can be produced by forming a perfluoro compound using various organic compounds as raw materials. For example, different halides can be used as raw materials as indicated by, for example:

$$C_mH_{2m+1}COX \quad [7]$$

or $$C_mF_{2m+1}COX' \quad [8]$$

(wherein, X and X' represent halogens and X≠X'). A perfluoro compound as indicated by the following formula [10] can be obtained in the form of a single product by forming a perfluoro compound as indicated by the following formula [9] from the raw material and subjecting to hydrolysis.

$$C_mF_{2m+1}COF \quad [9]$$

$$C_mF_{2m+1}COOH \quad [10]$$

In addition, in the production process indicated in the first embodiment, following formation of the perfluoro compound and purging fluorine gas from the reaction system, alcohol (ROH) may be added to transform to an ester followed by separation of a single perfluoro compound product from the reaction system.

In addition, in the production process indicated in the second embodiment, in the case of using for the raw material solution a perfluoro compound in which all of the plurality of groups thereof are sulfonyl groups, after purging fluorine gas from the reaction system by utilizing differences in reactivity, alcohol (ROH) may be added to transform the product to an ester followed by separating a single perfluoro compound product from the reaction system by distillation.

In addition, in the production process indicated in the second embodiment, the perfluoro compound having a plurality of polar groups used for dissolving the raw material and for the reaction solvent can be recovered and reused without modification.

According to the processes for producing fluorine-containing compounds indicated in the first and second embodiments, fluorination, and particularly perfluorination, of various organic compounds can be safely realized at high yield and without converting the structure of hydrocarbon compound raw materials. Thus, these processes can be widely used as production processes of pharmaceuticals, agricultural chemicals, polymers, functional products, surfactants, cleaners and various other chemical products and synthetic intermediates thereof.

EXAMPLES

The following provides a detailed explanation of the present invention through examples thereof. Furthermore, the present invention is not limited by these examples.

In addition, identification of reaction products in the following examples was carried out by GC-MS (EI), $^1$H (270 MHz, TMS standard)/$^{19}$F (254 MHz, CCl$_3$F standard)-NMR and FT-IR.

In addition, an apparatus equipped with a capillary column having an inner diameter of 0.25 mm and total length of 30 m (produced by J&W Co., DB-200) and an FID detector was used for gas chromatography (GC). Measurement results obtained by GC described in the examples refer to GC purity (or purity) (Area %).

In addition, yield was calculated using the value of GC measurement results (Area %).

First Embodiment

Example 1

Fluorination of Caprylyl Chloride (C$_7$H$_{15}$COCl)

<Step for Dissolving in Anhydrous Hydrofluoric Acid>

A fluororesin-coated stirrer was placed in a transparent fluororesin vessel having a volume of 7 ml and equipped with a nitrogen gas inlet tube followed by the addition of 1.5 g of anhydrous hydrofluoric acid and cooling with ice from the outside while stirring. 1.63 g (10 mmol) of caprylyl chloride were then dropped in over the course of about 10 minutes using a syringe followed by continuing to stir for an additional 20 minutes. The vessel was then removed from the ice bath and stirred for 2 hours at room temperature followed by concentrating the solution to obtain 2.13 g of a clear solution. In this step, caprylyl chloride is transformed to acid fluoride as indicated by the following formula [11]. The product was used in liquid-phase fluorination without purifying.

$$C_7H_{15}COCl + HF \rightarrow C_7H_{15}COF + HCl\uparrow \qquad [11]$$

<Liquid-Phase Fluorination> C$_7$H$_{15}$COF→C$_7$F$_{15}$COF

A fluororesin-coated PFA reactor having a volume of 180 ml was used equipped with a gas access port, a raw material inlet port, a 0° C. and −78° C. two-stage condenser (in which an NaF pellet filling tube and reaction liquid return line were installed between the condensers), a fluororesin-coated stirrer and an external temperature controller. 100 ml of perfluorohexane were charged into the reactor followed by bubbling nitrogen gas through the liquid for 0.5 hours at a flow rate of 3 L/hr.

Next, the nitrogen gas was replaced with a mixed gas consisting of 30% by volume of fluorine and 70% by volume of nitrogen, and this mixed gas was bubbled through the liquid for 0.5 hours at the rate of 3.2 L/hr to saturate the perfluorohexane with fluorine gas.

The anhydrous hydrofluoric acid solution of caprylyl chloride was transferred to a plastic syringe (total volume: 2.2 ml) and supplied over the course of 7 hours to the reaction vessel while maintaining bubbling of the mixed gas of 30% by volume fluorine and 70% by volume nitrogen (flow rate: 3.2 L/hr). The temperature of the reaction liquid was controlled to 27 to 28° C. Next, 0.56 g (3 mmol) of hexafluorobenzene were dissolved in the perfluorohexane and brought to a final volume of 10 ml, and a mixed gas of 30% by volume fluorine and 70% by volume nitrogen was supplied over the course of 2 hours while bubbling at a flow rate of 1.34 L/hr. Subsequently, the mixed gas was replaced with nitrogen gas to purge the reaction liquid of fluorine gas by bubbling through the reaction liquid for 1 hour at a flow rate of 3 L/hr. The temperature of the reaction liquid was controlled to 23 to 25° C.

<Esterification>  C$_7$F$_{15}$COF+CH(CH$_3$)$_2$OH→C$_7$F$_{15}$COOCH(CH$_3$)$_2$ Esterification was carried out by controlling the temperature of the reaction liquid to 20° C., adding 1.2 g (20 mmol) of anhydrous isopropyl alcohol and stirring for 1 hour. Next, the reaction liquid was washed with water and dried with anhydrous magnesium sulfate. Following concentration, the residue was further subjected to vacuum distillation to fractionate into a fraction from 69° C./15 mmHg to 71° C./15 mmHg and obtain 1.82 g of C$_7$F$_{15}$COOCH(CH$_3$)$_2$. Purity as determined by gas chromatography was 94.73% and yield was 38%. The results of identification were as indicated below.

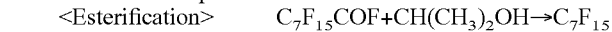

$^1$H-NMR (solvent: CDCl$_3$, ppm): 5.25(m,1H), 1.36(d,6H)

$^{19}$F-NMR (solvent: CDCl$_3$, ppm): −81.4(t,F), −119.2(m, 2F), −122.0(d,2F), −122.5(s,2F), −123.1(q,4F), −126.6(m, 2F)

Example 2

The same procedure as Example 1 was carried out with the exception of changing the flow rate of the bubbled mixed gas of 30% by volume fluorine and 70% by volume nitrogen to 3.97 L/hr, adding 0.16 g (2 mmol) of benzene to the raw material solution and dissolving therein (total volume: 2.6 ml), and supplying the resulting solution to obtain 2.96 g of C$_7$F$_{15}$COOCH(CH$_3$)$_2$. GC purity was 95.22% (yield: 62%).

Example 3

Fluorination of Sebacoyl Chloride (ClCO(CH$_2$)$_8$COCl)

<Dissolution in Anhydrous Hydrofluoric Acid>

The same procedure as Example 1 was carried out using the same apparatus as Example 1 with the exception of changing the amount of HF to 2.0 g and changing the raw material to 2.39 g (10 mmol) of sebacoyl chloride to obtain 2.92 g of a clear solution.

In this step, acid chloride was substantially transformed to acid fluoride according to the reaction of formula [12].

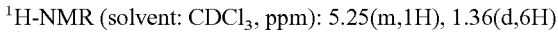
$$ClCO(CH_2)_8COCl \rightarrow FCO(CH_2)_8COF \qquad [12]$$

The product was used in liquid-phase fluorination without purifying.

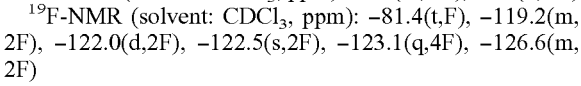
<Liquid-Phase Fluorination> FCO(CH$_2$)$_8$COF→FCO(CF$_2$)$_8$COF

A mixed gas of fluorine at 30% by volume and nitrogen at 70% by volume was used at a flow rate of 2.08 L/hr and the amount of benzene added to the raw material hydrofluoric acid solution was 0.31 g (4 mmol). The same reaction and procedure as Example 2 were carried out with the exception of supplying the raw material over the course of 8 hours and controlling the temperature of the reaction solution to 23 to 26° C.

<Esterification> FCO(CF$_2$)$_8$COF+2CH(CH$_3$)$_2$OH→(CH$_3$)$_2$CHOCO(CF$_2$)$_8$COOCH(CH$_3$)$_2$ The same reaction and procedure as Example 2 were carried out with the exception of changing the amount of anhydrous isopropyl alcohol to 2.4 g (40 mmol). Following concentration, the residue was further subjected to vacuum distillation to fractionate a fraction from 100° C./5 mmHg to 105° C./5 mmHg and obtain 3.00 g of (CH$_3$)$_2$CHOCO(CF$_2$)$_8$COOCH(CH$_3$)$_2$. GC purity was 89.67% and yield was 52%. The results of identification were as indicated below.

$^1$H-NMR (solvent: CDCl$_3$, ppm): 5.25(m,2H), 1.36(d, 12H)

$^{19}$F-NMR (solvent: CDCl$_3$, ppm): −119.2(t,4F), −122.1(d, 8F), −123.1(d,4F)

Example 4

Fluorination of Suberoyl Chloride (ClCO(CH$_2$)$_6$COCl)

<Dissolution in Anhydrous Hydrofluoric Acid Solution>

The same procedure as Example 1 was carried out using the same apparatus as Example 1 with the exception of changing the amount of anhydrous hydrofluoric acid to 1.5 g and changing the raw material to 2.11 g (10 mmol) of suberoyl chloride to obtain 2.32 g of a clear solution.

In this step, acid chloride was substantially transformed to acid fluoride according to the reaction of formula [13].

ClCO(CH$_2$)$_6$COCl→FCO(CH$_2$)$_6$COF   [13]

The product was used in liquid-phase fluorination without purifying.

<Liquid-Phase Fluorination/Esterification>

The flow rate of mixed gas of fluorine at 30% by volume and nitrogen at 70% by volume was changed to 2.53 L/hr and the amount of benzene added to the raw material solution was changed to 0.23 g (4 mmol). The raw material was supplied over the course of 8 hours and the temperature of the reaction liquid was controlled to 26 to 27° C. Moreover, the same reaction and procedure as Example 1 were carried out with the exception of changing the conditions of the subsequent reaction using hexafluorobenzene to a mixed gas of fluorine at 20% by volume and nitrogen at 80% by volume, flow rate of 2.02 L/hr and temperature of 19 to 21° C. to fluorinate the FCO(CH$_2$)$_6$COF and obtain FCO(CF$_2$)$_6$COF.

<Esterification>

The same reaction and procedure as Example 1 were carried out with the exception of using anhydrous methyl alcohol for the alcohol, and following concentration, the residue was further subjected to vacuum distillation to fractionate a fraction from 106° C./11 mmHg to 108° C./11 mmHg and obtain 2.23 g of H$_3$CCO(CF$_2$)$_6$COOCH$_3$. GC purity was 94.55% and yield was 51%. The results of identification were as indicated below.

$^1$H-NMR (solvent: CDCl$_3$, ppm): 3.99(s,6H)

$^{19}$F-NMR (solvent: CDCl$_3$, ppm): −118.9(m,4F), −122.2(m,4F), −123.2(m,4F), Example 5

Fluorination of Adipoyl Chloride (ClCO(CH$_2$)$_4$COCl)

<Dissolution in Anhydrous Hydrofluoric Acid>

The same procedure as Example 1 was carried out using the same apparatus as Example 1 with the exception of changing the amount of anhydrous hydrofluoric acid to 1.57 g and changing the raw material to 1.83 g (10 mmol) of adipoyl chloride to obtain 2.24 g of a clear solution (FCO(CH$_2$)$_4$COF).

<Liquid-Phase Fluorination>

The flow rate of mixed gas of fluorine at 30% by volume and nitrogen at 70% by volume was changed to 1.77 L/hr and the amount of benzene added to the raw material solution was changed to 0.23 g (3 mmol). The raw material was supplied over the course of 8 hours, the temperature of the reaction liquid was controlled to 25 to 27° C., and the same reaction and procedure as Example 1 were carried out with the exception of not using hexafluorobenzene to fluorinate the FCO(CH$_2$)$_4$COF and obtain FCO(CF$_2$)$_4$COF.

<Esterification>

The same reaction and procedure as Example 1 were carried out with the exception of using anhydrous methyl alcohol for the alcohol, and following concentration, the residue was further subjected to vacuum distillation to fractionate a fraction from 89° C./11 mmHg to 91° C./11 mmHg and obtain 1.68 g of H$_3$CCO(CF$_2$)$_4$COOCH$_3$. GC purity was 92.34% and yield was 49%. The results of identification were as indicated below.

$^1$H-NMR (solvent: CDCl$_3$, ppm): 3.98(s,6H)

$^{19}$F-NMR (solvent: CDCl$_3$, ppm): −119.1(m,4F), −123.2(m,4F)

Second Embodiment

Example 6

Fluorination of Caprylyl Chloride (C$_7$H$_{15}$COCl)

<Liquid-Phase Fluorination> C$_7$H$_{15}$COCl→C$_7$F$_{15}$COF 1.63 g (10 mmol) of caprylyl chloride were put into a glass vessel followed by the addition of FO$_2$S(CF$_2$)$_3$SO$_2$F, dissolving therein and bringing to a final volume of 6 ml (raw material solution). 100 ml of perfluorohexane were charged into a similar reactor as that used in Example 1 followed by bubbling nitrogen gas through the solution for 0.5 hours at a flow rate of 3 L/hr. Next, the nitrogen gas was replaced with a mixed gas of fluorine at 20% by volume and nitrogen at 80% by volume, and the mixed gas was bubbled through the solution for 0.5 hours at a flow rate of 3.9 L/hr to saturate the perfluorohexane with fluorine gas. The raw material solution was supplied over the course of 6 hours using a syringe pump to the reaction vessel while maintaining bubbling of the mixed gas of 20% by volume fluorine and 80% by volume nitrogen. The temperature of the reaction liquid was controlled to 24 to 26° C. Next, 0.93 g (5 mmol) of hexafluorobenzene were dissolved with perfluorohexane and brought to a final volume of 10 ml followed by supplying over the course of 1 hour while bubbling the mixed gas of 20% by volume of fluorine and 80% by volume of nitrogen at the rate of 1.89 L/hr. The temperature of the reaction liquid was controlled to 23 to 24° C., and this procedure was repeated twice. Subsequently, the mixed gas was replaced with nitrogen gas and the reaction liquid was purged of fluorine by bubbling the nitrogen gas through the reaction liquid for 1 hour at a flow rate of 2.23 L/hr.

<Esterification> C$_7$F$_{15}$COF+(CH$_3$)$_2$CHOH→C$_7$F$_{15}$COOCH(CH$_3$)$_2$ Esterification was carried out by controlling the temperature of the reaction liquid to 20° C., adding 1.8 g (30 mmol) of anhydrous isopropyl alcohol and stirring for 1 hour. The reaction liquid was washed with water and dried with anhydrous magnesium sulfate. Following concentration, the residue was further subjected to vacuum distillation to fractionate a fraction at about 90° C./15 mmHg and obtain 3.67 g of $C_7F_{15}COOCH(CH_3)_2$. Purity as determined by gas chromatography was 88.29% and yield was 71%. The results of identification were as indicated below.

$^1$H-NMR (solvent: CDCl$_3$, ppm): 5.25(m,1H), 1.36(d,6H)
$^{19}$F-NMR (solvent: CDCl$_3$, ppm): −81.4(t,3F), −119.2(m, 2F), −122.0(d,2F), −122.5(s,2F), −123.1(q,4F), −126.6(m, 2F)

Example 7

Fluorination of Caprylyl Chloride ($C_7H_{15}COCl$)

0.82 g (5 mmol) of caprylyl chloride were dissolved in $FO_2S(CF_2)_3SO_2F$ and brought to a final volume 20 ml. The perfluorohexane was changed to 80 ml of $FO_2S(CF_2)_3SO_2F$ and the flow rate of a mixed gas of 30% by volume fluorine and 70% by volume nitrogen was changed to 3 L/hr. 0.47 g (2.5 mmol) of hexafluorobenzene were dissolved in the $FO_2S(CF_2)_3SO_2F$ and brought to a final volume of 5 ml followed by supplying the mixed gas of 30% by volume fluorine and 70% by volume nitrogen used during fluorination for 2 hours at a flow rate of 2.23 L/hr. 0.6 g (10 mmol) of anhydrous isopropyl alcohol were used for the alcohol. Other embodiments of the reaction and procedure were the same as Example 6. After concentrating the reaction liquid, the reaction liquid was subjected to vacuum distillation and the target compound of [$C_7F_{15}COOCH(CH_3)_2$] was confirmed to be present in the resulting fraction at a yield of 55%.

The invention claimed is:

1. A process for producing perfluoro compounds, comprising:
    liquid-phase fluorination by introducing a raw material compound and fluorine gas into a liquid-phase fluorination solvent to replace hydrogen atoms in the raw material compound with fluorine atoms;
    wherein, the raw material compound is at least one of components selected from a group consisting of aromatic hydrocarbons, alcohols, ethers, organic acids, esters, and acid halides,
    fluorination is promoted by dissolving the raw material compound in anhydrous hydrofluoric acid and introducing into the liquid-phase fluorination solvent, after preliminarily dissolving fluorine gas in the liquid-phase fluorination solvent, and
    thereby producing the perfluoro compound having the formula (9):

$$C_mF_{2m+1}COF \qquad (9).$$

2. A process for producing perfluoro compounds, comprising:
    liquid-phase fluorination by introducing a raw material compound and fluorine gas into a liquid-phase fluorination solvent to replace hydrogen atoms in the raw material compound with fluorine atoms;
    wherein, the raw material compound is at least one of components selected from a group consisting of alkanes, cycloalkanes, aromatic hydrocarbons, alcohols, ethers, organic acids, esters and acid halides,
    fluorination is promoted by dissolving the raw material compound in a raw material solution comprising a perfluoro compound having a plurality of carbonyl groups or sulfonyl groups in a molecule thereof and introducing into the liquid-phase fluorination solvent, after preliminarily dissolving fluorine gas in the liquid-phase fluorination solvent, and
    thereby producing the perfluoro compound having the formula (9):

$$C_mF_{2m+1}COF \qquad (9).$$

3. The process for producing perfluoro compounds according to claim 2, wherein the raw material solution comprises at least one of an XOCYCOX, XO$_2$SYCOX or XO$_2$SYSO$_2$X compound (wherein, X represents a halogen and Y represents a linear or branched perfluoroalkylene group).

4. The process for producing perfluoro compounds according to claim 1, wherein the liquid-phase fluorination solvent is a perfluorohydrocarbon solvent (which may contain heteroatoms in a molecule thereof).

5. The process for producing perfluoro compounds according to claim 2, wherein the liquid-phase fluorination solvent is a perfluoro compound having a plurality of polar groups in a molecular thereof.

6. The process for producing perfluoro compounds according to claim 1,
    wherein the liquid-phase fluorination is carried out in the presence of a linear, branched or cyclic hydrocarbon compound (which may contain a heteroatom in a molecule thereof) having 1 or more unsaturated bonds or 1 or more C—H bonds in a molecule thereof and having 5 or more carbon atoms and 30 or less carbon atoms.

7. The process for producing perfluoro compounds according to claim 1, wherein the raw material compound is an organic acid or organic acid halide.

8. The process for producing perfluoro compounds according to claim 2, wherein the liquid-phase fluorination solvent is a perfluorohydrocarbon solvent (which may contain heteroatoms in a molecule thereof).

9. The process for producing perfluoro compounds according to claim 2,
    wherein the liquid-phase fluorination is carried out in the presence of a linear, branched or cyclic hydrocarbon compound (which may contain a heteroatom in a molecule thereof) having 1 or more unsaturated bonds or 1 or more C—H bonds in a molecule thereof and having 5 or more carbon atoms and 30 or less carbon atoms.

10. The process for producing perfluoro compounds according to claim 2, wherein the raw material compound is an organic acid or organic acid halide.

* * * * *